United States Patent [19]
Brizgys et al.

[11] Patent Number: 5,807,752
[45] Date of Patent: Sep. 15, 1998

[54] ASSAY USING AN UNBLOCKED SOLID PHASE WITH IMMOBILIZED ANALYTE BINDING PARTNER

[75] Inventors: Marius Brizgys; Bernd Hilger; James C. D. Hengst; David Webster; Harvey Buck, all of Indianapolis, Ind.

[73] Assignee: Boehringer Mannheim Corporation, Indianapolis, Ind.

[21] Appl. No.: 943,897

[22] Filed: Sep. 11, 1992

[51] Int. Cl.⁶ .................. G01N 33/543; G01N 33/546; G01N 33/558; G01N 33/553

[52] U.S. Cl. .................. 436/513; 435/7.94; 435/7.92; 435/805; 435/810; 436/514; 436/524; 436/528; 436/533

[58] Field of Search ............... 435/7.94, 7.92, 435/7.1, 975, 810, 7.4, 960, 962; 436/513, 514, 530, 533, 512, 528, 524

[56] References Cited

U.S. PATENT DOCUMENTS

| | | | |
|---|---|---|---|
| 4,703,017 | 10/1987 | Campbell et al. | 436/501 |
| 4,727,037 | 2/1988 | Ring | 436/548 |
| 4,962,023 | 10/1990 | Todd | 435/7.92 |
| 5,047,325 | 9/1991 | Pronovost et al. | 435/7.36 |
| 5,047,326 | 9/1991 | Pronovost | 435/7.36 |
| 5,075,078 | 12/1991 | Osikowicz | 422/56 |
| 5,081,010 | 1/1992 | Cummins et al. | 435/5 |
| 5,106,758 | 4/1992 | Adler et al. | 435/7.1 |
| 5,122,452 | 6/1992 | Yamazaki et al. | 435/7.92 |
| 5,149,623 | 9/1992 | Carlson | 435/5 |
| 5,169,756 | 12/1992 | Ranbyeral | 435/7.92 |
| 5,169,757 | 12/1992 | Yamazaki et al. | 435/7.92 |
| 5,200,317 | 4/1993 | Georgevich | 435/7.4 |
| 5,290,678 | 3/1994 | Jackowski | 435/7.4 |

OTHER PUBLICATIONS

Kenna et al (1985) J. Immunol Methods 85:409–419.
Katus et al., Development and In Vitro Characterization of a new Immunoassays of Cardiac Troponin T:, Clin. Chem. 38(3): 387–393 (Mar., 1992).

*Primary Examiner*—James C. Housel
*Assistant Examiner*—Nancy J. Parsons
*Attorney, Agent, or Firm*—Felfe & Lynch

[57] ABSTRACT

The invention relates to a test system useful in carrying out diagnostic assays. One component of the test system is an unblocked solid phase test carrier with a three dimensional configuration, impregnated with a first binding partner for analyte of interest. The second component of a binding agent containing a second binding partner coupled to an immediately visually determinable label, and a blocking agent. Rapid and accurate assays may be carried out by using the described system.

43 Claims, 2 Drawing Sheets

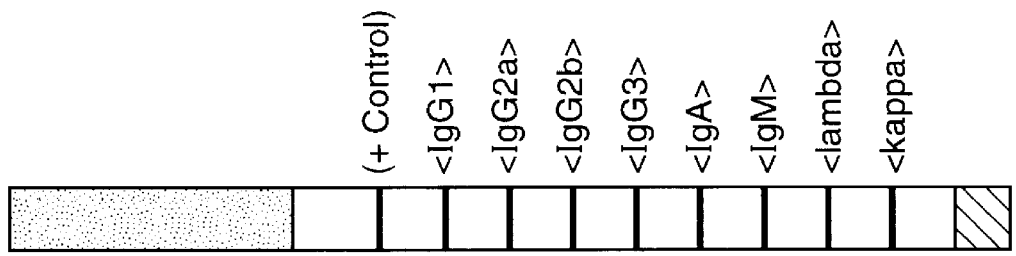
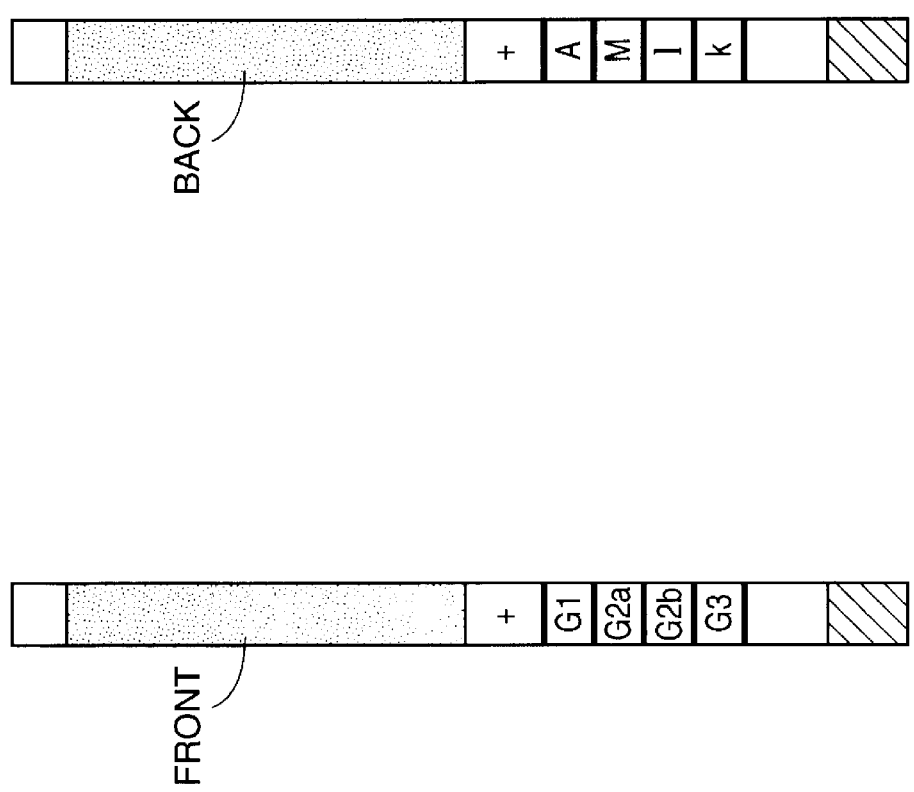

ASSAY USING AN UNBLOCKED SOLID PHASE WITH IMMOBILIZED ANALYTE BINDING PARTNER

FIELD OF THE INVENTION

This invention relates to the field of immunodiagnosis. More particularly, it relates to the determination of one or more analytes, or characteristics thereof, via analysis of a sample with a particular test device.

BACKGROUND AND PRIOR ART

The field of immunology has been adopted for use in analyte determination in a number of ways. Of particular interest to the invention described herein is the use of principles of immunology to determine analytes or characteristics thereof.

Clinical diagnosis exploits the well known ability of an antibody to bind to a molecule for which it is specific. The resulting complex of "probe" and "target" (terms used for reasons explained infra) can be determined in a number of ways. One family of diagnostic methodologies, the "homogeneous assays", take place in solution, and is not of particular pertinence to the invention described herein. The family of heterogeneous assays is of pertinence.

In a heterogeneous assay, there is some change in phase, or a separation of phases which takes place in order to identify and/or quantify a target material. The change in phase can involve, e.g., the binding of the target molecule to a solid phase bound probe. Once the binding takes place, the solid phase bound complex is identified, frequently by contact with a second, target specific labeled probe. The label on the probe may be chosen from a number of options which include enzymes, fluorescent molecules, radiolabels and so forth. Once the labeled probes bind to the target molecule on the solid phase, it is general practice to remove labeled probe not bound to target, but still associated with the solid phase. Generally, this is accomplished by washing the solid phase. This step is necessary, but time consuming. In addition, washing introduces an element of inaccuracy as one must be concerned either with not washing the solid phase thoroughly enough, or washing it too thoroughly, thereby displacing target bound material. Either situation introduces uncertainty in the measurement, and a need to run a control.

While certain forms of label have become commonplace in the field, they are not without their problems. Radiolabels, for example, presuppose a site on the probe to which they can bind. Assuming such a site exists, radiolabels must be handled with care, and require skilled personnel. Enzymes have probably become the most common labels. Assays involving such labels require the use of a substrate for the enzyme. Upon contact, the substrate is acted upon, and generates a detectable signal. Generally the signal is a color or a change in color. While such systems are easier to work with than radiolabels, the reaction between enzyme and substrate can be time consuming. Also, enzymes deteriorate over time, and test systems using them have limited shelf lives.

Additional labels have also been developed, such as fluorescent dyes and magnetic microparticles, but none have proven to be entirely satisfactory. Development of a suitable system requires the consideration of a number of features, including the length of time to carry out the assay, the equipment required, stability of the reagents, and so forth.

Previously, the reaction at the heart of all immunodiagnostics was referred to as one between target and probe. This language is used because the "target" may be any of a number of substances. Specific biological materials, such as hormones, cytokines, glycoproteins, etc., have all been determined via immunodiagnostics, as have cell types, viruses, antibodies, bacteria, and other materials. When the term analyte is used hereafter, it is intended to embrace all entities which may be determined via immunodiagnostic methodologies.

The probe substance is the material which binds to the analyte of interest. Frequently, but not always, this probe is an antibody, be it polyclonal or monoclonal. The probe may also be an antibody fragment which is also capable of binding to an analyte, such as Fab fragment. When the analyte is itself an antibody, the probe may be an antibody as well, but it may also be an analyte, or analyte fragment which binds to the target antibody. For convenience, the probe will be referred to as a receptor thereafter.

The type of assay involved in the invention described herein is a subgroup of heterogeneous assay, referred to as a sandwich assay. This type of assay involves formation of a solid phase bound complex of at least three members. When only three members are involved, the analyte is at the center, flanked by a solid phase bound to capture receptor, and a labeled receptor. These are referred to hereinafter as first and second receptor.

Adaptation of sandwich assays for heterogeneous determination of an analyte is not new. Examples of such assays may be found in, e.g., U.S. Pat. No. 4,727,037 to Ring, and U.S. Pat. No. 4,703,017 to Campbell et al. The Ring patent teaches a device and method for isotyping antibodies (i.e., determining heavy and light chains of antibodies in a sample). Receptor antibodies are immobilized onto a membrane, and sample and membrane are combined and incubated. Following washing, an enzyme labeled antibody is added, followed by addition of enzyme substrate. The assay requires less than two hours to carry out. The Campbell patent teaches similar test systems, also using the dot blot methodology. Liposomes labeled receptors are used, where the liposomes contain a dye, such as rhodamine.

In carrying out immunodiagnostic assays, the art is familiar with the use of blocking agents prior to the running of the actual assay. Blocking agents are used to treat the test carrier so that any portions of the strip which do not contain analyte specific reagents are "blocked" thereby preventing non-specific binding with the analyte of interest.

Blocking agents and their use are described in, e.g., European Patent Application 291194 and 299428. In each case, prior to carrying out the assay, the strip is dipped into solution of blocking agent, followed by rinsing and drying. These steps add a minimum of 30 minutes to the assay. In U.S. Pat. No. 4,727,037, the blocking step requires overnight incubation with a solution of bovine serum albumin (BSA) in PBS. U.S. Pat. No. 4,703,017, also requires from 30 minutes to one hour for blocking, again using BSA. The blocking step adds a great deal of time to the assay, as well as additional steps and reagents.

It is desirable to have a test system available which dispenses with the need to preincubate the test carrier with a blocking agent, so as to drastically shorten the time required to run a test assay; however, the resulting system must still provide accurate results. The inventors have found, surprisingly, that the blocking step, previously though necessary, can be eliminated. As a result, assays can be run to completion in as little as five minutes.

SUMMARY OF THE INVENTION

The invention is based upon the surprising discovery that a test system utilizing two analyte specific binding partners can be prepared, where the blocking agent can be combined with the second binding partner and used in concert therewith, rather than in a separate time consuming step. As a result, the assays of the invention can be carried out in as little as five minutes, and a separate blocking step is not necessary.

The following detailed description shows the efficacy of the invention.

BRIEF DESCRIPTION OF THE FIGURES

FIG. 1 shows the front and back of a typical isotyping strip in accordance with the invention.

FIG. 2 displays how an isotyping strip in accordance with the invention appears from its top face.

DETAILED DESCRIPTION OF PREFERRED EMBODIMENTS

Figure 3:
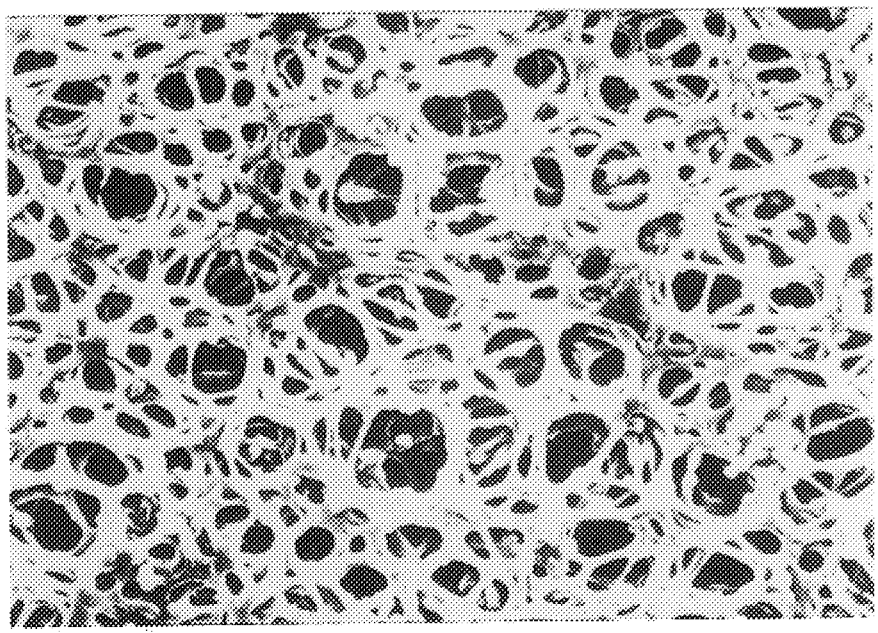
FIG. 3 is a scanning microscope photograph top view of a test strip prepared in accordance with the invention.

The invention is a test system useful for determining one or more analytes in a sample. The system contains at least two elements. The first element is a carrier, which is porous, and has contained therein a requisite number of receptors or binding partners specific for the analyte or analytes to be determined. The binding partner or partners are positioned on the porous test carrier in a defined, spatial array, such as the horizontal lines of FIG. 1.

The second element of the test system is a labelled receptor or binding partner for the analyte to be determined, combined with a blocking agent. The labelled receptor is labelled with an immediately visually detectable label, and binds to the analyte on the test carrier, thereby marking the site of binding with a directly determinable signal.

"Immediately visually detectable" and "directly detectable" as used herein mean that the binding can be determined with the naked eye immediately after the reaction takes place, and without the need for additional reaction steps, washing, or equipment. Thus, the label may be a metal particle of visually determinable size such as a gold sol, or a colored latex particle, the latter being especially preferred. The latex particles preferably have an average diameter of 0.1 to 0.4 $\mu$m, an average diameter of about 0.2 $\mu$m being especially preferred. Immediately visually detectable do not include enzymes, fluorescent molecules, indicators which require mordanting for visualization, or any material which is not immediately determinable to the naked eye.

In particularly preferred embodiments, the test system is one which can be used for isotyping antibodies. The system may also be used for distinguishing between isotypes of proteins that are not antibodies, such as enzyme isotypes or other protein isotypes. Examples of these molecules include the creatine kinase and alkaline phosphatase family of enzymes, both of which are known to contain various isoforms, and isoforms of proteins such as troponin T. The importance of determining isoforms of this latter protein may be seen in, e.g. Katus et al., Clin. Chem. 38(3): 386–393 (1992).

The porous test carrier of the invention may be made of any of the materials known to the art to be useful in test strip manufacture. Examples of useful materials are nitrocellulose paper or other cellulose derivatives, nylon membranes, and so forth. The pore size of the absorbent paper preferably averages anywhere from about 1 $\mu$m to about 12 $\mu$m in diameter, 5 $\mu$m diameter being particularly preferred. A preferred range for the pores is from 3–10 $\mu$m.

In an especially preferred embodiment, two strips of porous material are bound together to form a front and back, each of which contains a pertinent immunoreactant. These materials are joined by any of the means known in the art for preparing a two sided strip, lamination being particularly preferred.

It is desirable, although not necessary, that the test carrier accommodate a wicking means at one end, and a waste means or "sink" at the other. The former feature acts to draw liquid into the portion of the carrier which contains capture receptor. The latter acts to drain liquid through the device, thereby facilitating the natural chromatographic properties of the device.

The capture receptors are impregnated on the device via any of the means known for incorporating immunoreactants into a carrier. In a particularly preferred embodiment, the test carrier material selected is such that capture receptor is impregnated therein at a concentration of from about 0.05 to about 0.10 $\mu$g per cm$^2$. "Impregnation" as used herein refers to the placement of the binding partner throughout the three dimensional configuration of the test carrier. This is important, because in prior art systems, such as those in U.S. Pat. No. 4,703,017 to Campbell, e.g., labelled reagents are concentrated on the top and bottom surfaces of the carrier, but do not penetrate into the actual internal matrix of the carrier. As such, prior art devices are better described as two dimensional carriers rather than the three dimensional carriers of the invention. Even at such low densities, the test carriers of the invention perform in a more than adequate manner.

The second portion of the test system, the labelled receptor, may be any of the various reactants listed supra, coupled to any of the immediately detectable labels known to the art. Both the capture and labeled receptors may be antibodies, antigens, protein A, (strept)avidin or any reactive portion thereof. Antibodies are preferred, most preferred being polyclonal antibodies. The labeled receptors may differ from each other or only a single type of labeled receptor need be used.

The second binding partner or receptor is combined with a blocking agent. As indicated previously, it is the function of blocking agents to prevent improper binding of receptor/binding partner to the test carrier. These agents have always been added prior to the addition of the second receptor, and thus this feature of the invention is in marked contrast to the prior art. The blocking agent used may be any of those well known to the art, such as polyethylene glycol or bovine serum albumin, the former being especially preferred.

Assays carried out in accordance with the invention take place in much less time than those of the prior art. The elimination of the blocking step is one reason for this, and one can secure an accurate reading in as little as less than five minutes. As will be seen in the non-limitative examples which follow, test systems in accordance with the invention are uniquely suitable for carrying out immunodiagnostic assays.

EXAMPLE 1

A series of porous test carriers were prepared by laminating a strip of microporous, nitrocellulose membrane (Schleicher & Schull, AE-98) onto an inert backing. A wick comprised of a polyester blend with cellulose paper and a reservoir of a chromatographic cellulosic paper (31-ET; Whatman Specialty Products), were attached to the strip. Samples of specific goat antimouse antibodies of heavy chain and light chain specificities (IgG1, IgG2a, IgG2b, IgG3, IgA, IgM, kappa, lambda), were equilibrated in 50 mM of 3-[N-morpholino]-2-hydroxy propanesulfonic acid ("MOPSO"), pH 7.2, containing 150 mM NaCl. The samples were then dispensed onto the microporous carrier, in amounts of approximately 125–250 ng, at a rate of 1.26 ul/cm, in the form of a line. Four analyte specific antibodies and one control, for a total of five lines, were applied to each side of the strip. Strips were then air dried at room temperature for fifteen minutes.

A binding reagent was prepared by combining labeled, second antibodies against specific heavy or light chains, and blocking agent. The second-antibodies were covalently linked to carboxylated, blue latex beads having an average size of 220 nm. The blocking agent was a buffer solution containing 1% polyethylene glycol 20,000. Blocking agent and labelled second antibody were combined, and lyophilized. The reagent was resolubilized by samples which, for this example, were murine monoclonal antibodies of known heavy and light chains, diluted in phosphate buffered saline solution.

A 150 ul aliquot of sample was added, in each case, to a 10×75 mm test tube containing lyophilized binding agent. The mixture was allowed to chromatograph up the strip, and intense lines were observed in less than five minutes. In each case, the pattern of staining indicated that the proper heavy or light chain had been identified.

EXAMPLE 2

Mouse ascites samples were assayed in the same manner as that described in example 1, the only difference being that ascites fluid was diluted in a range of 1:10,000–1:50,000 with PBS and 150 ul of the mixture was added to test tubes. Again, accurate results were secured in less than five minutes.

EXAMPLE 3

Mouse culture supernatant was tested in the same manner as the samples of examples 1 and 2. The supernatant was diluted to a range of 1:50–1:100 with PBS and all other steps were as described supra. Again, accurate results were obtained in less than five minutes.

EXAMPLE 4

Samples of purified mouse antibody were tested by diluting these to a range of 0.01–1 ug/ml with PBS, and assaying as above. Again, all results were obtained in less than five minutes, and were accurate.

EXAMPLE 5

The distribution of first binding partner throughout the test carriers was studied. To do this, carriers prepared in the manner described in Example 1 were subjected to electron microscopy. The study revealed that the carrier had pores ranging in diameter from about 1 to about 10 um.

Latex particles were observed to be distributed throughout the carrier, rather than just on the top and bottom surfaces. Thus, it may be said that they have impregnated the three dimensional array.

Calculations were carried out to determine the amount of open space in the carrier. This was found to be about 24%. Further calculations indicate that the binding partners were distributed throughout the three dimensional array in a range of from about 0.05 ug to about 0.10 ug/cm$^2$.

It will be seen that the invention discloses a unique and useful test system for determining an analyte or analytes. In one broad embodiment, the test system comprises two components. The first is a test carrier, which must be porous, and which contains, impregnated therein, a first binding partner for an analyte of interest. This first binding partner is placed on the carrier in a defined, predetermined array. This can be a line, a circle, a dot, or any figure desired, such that when the test is completed, the artisan can detect the results immediately. As indicated supra, various cellulose and nitrocellulose papers and membranes are preferred as the test carrier, these having pore sizes in the ranges set forth above.

The second component of the test system is a binding reagent. This component contains the second binding partner, coupled to the immediately visually detectable label, together with the blocking agent. This combination may be, but need not be, lyophilized. Solutions, powders, tablets, etc., are all possible formulations of the binding reagent.

The binding partners may be any substances which bind to the analyte of interest, antibodies and fragments of antibodies being especially preferred.

The test systems of invention, as indicated, may be used to identify particular analytes, and may also be used to identify different types of forms of a generic class of analytes, such as in antibody typing. When test systems are prepared to determine single analytes, of course there need only be one type of first binding partner and impregnated in the device and one type of second binding partner in the binding reagent. This number increases in the case of distinguishing different types or forms of analyte. For example, in a universal antibody isotype determination strip, binding partners for IgA, IgD, IgE, IgM, and all forms of IgG (IgG1, IgG2a, IgG2b, IgG3) will be present, as well as binding partners for both kappa and lambda light chains. Usually, however, such complete determination is not necessary, and one may conveniently delete, e.g., IgD and IgE specific binding partners from the strip. In addition to antibody isotype differentiation, isoforms of various proteins, including enzymes, such as creatine kinase, may be assayed using the test systems of the invention. Routine modification of the methodology set forth for preparing antibody isotype strips accomplishes this. Further elaboration is not necessary, as the foregoing disclosure may easily be adapted by the skilled artisan to prepare the desired test system. As such, the test systems of the invention may be used in, e.g., study of cardiac function and irregularities by determining proteins associated therewith. Examples of such proteins include, e.g., isoforms of troponin, such as troponin T.

It will be understood that the specification and examples are illustrative but not limitative of the present invention and that other embodiments within the spirit and scope of the invention will suggest themselves to those skilled in the art.

We claim:

1. Test system useful in determining an analyte, comprising:
   (a) a porous nitrocellulose test carrier, untreated with a blocking agent, having a three dimensional configuration which has impregnated therein a first binding partner specific for said analyte, said first binding partner being impregnated in a defined, spatial array, and;
   (b) a binding reagent which comprises, in combination:
      (i) a second binding partner linked to a particle of sufficient size to be immediately visually detectable by the naked eye, wherein said second binding partner binds to said analyte, and
      (ii) a blocking agent.

2. The test system of claim 1, wherein said porous nitrocellulose test carrier has incorporated therein a plurality of different first binding partners, each of which specifically binds to a different specific analyte, and said binding reagent comprises a plurality of different second binding partners, each of which is linked to an immediately visually detectable particle, and each of which specifically binds to a different analyte.

3. The test system of claim 1, wherein said immediately visually detectable particle is a colored particle.

4. The test system of claim 3, wherein said colored particle is a latex particle.

5. The test system of claim 1, wherein said second binding partner is an antibody.

6. The test system of claim 1, wherein said first binding partner is an antibody.

7. The test system of claim 1, wherein said immediately detectable particle is a metal particle.

8. The test system of claim 7, wherein said metal particle is a gold particle.

9. The test system of claim 1, wherein said binding reagent is in the form of a solution.

10. The test system of claim 1, wherein said binding reagent is in the form of a lyophilisate.

11. The test system of claim 1, wherein said first binding partner is an antibody or analyte specific antibody fragment.

12. The test system of claim 1, wherein said second binding partner is an antibody or analyte specific antibody fragment.

13. The test system of claim 1, wherein said porous nitrocellulose carrier comprises pores having an average diameter of from about 1 um to about 12 um.

14. The test system of claim 13, wherein said pores have an average diameter of from about 3 um to about 10 um.

15. The test system of claim 14, wherein said pores have an average diameter of about 5 um.

16. The test system of claim 1, wherein said first binding partner is impregnated in said porous nitrocellulose test carrier at a density of from about 0.05 ug to about 0.10 ug/cm$^2$ of surface area of said three dimensional configuration.

17. The test system of claim 2, wherein said plurality of different first binding partners comprises at least two antibody heavy chain specific binding partners.

18. The test system of claim 17, further comprising at least one light chain specific binding partner.

19. The test system of claim 17, wherein said plurality of different first binding partners comprise IgA, IgD, IgE, IgG and IgM specific binding partners.

20. The test system of claim 19, said plurality of different first binding partners further comprising kappa chain and lambda chain specific binding partners.

21. The test system of claim 2, wherein said porous nitrocellulose test carrier has a front side and a back side, and each side is impregnated with at least one first binding partner.

22. The test system of claim 2, wherein each of said plurality of different first binding partners specifically binds to a protein isoform.

23. The test system of claim 22, wherein said protein isoform is an enzyme isoform.

24. The test system of claim 22, wherein said protein isoform is an isoform characteristic of a cardiac irregularity.

25. The test system of claim 23, wherein said enzyme isoform is a creatine kinase isoform.

26. The test system of claim 1, wherein said first binding partner specifically binds to an isoform of troponin.

27. The test system of claim 26, wherein said troponin is troponin T.

28. The test system of claim 1, wherein said blocking agent is a polyethylene glycol.

29. Method for determining an analyte comprising:
(a) combining a sample containing said analyte with a binding reagent, said binding reagent comprising, in combination
    (i) a second binding partner linked to a particle which is immediately visually detectable by the naked eye, wherein said second binding partner binds to said analyte, and
    (ii) a blocking agent, to form a mixture;
(b) contacting said mixture to a porous nitrocellulose test carrier having a three dimensional configuration and having impregnated therein a first binding partner specific for said analyte, said binding partner being impregnated in a defined spatial array wherein said porous nitrocellulose test carrier has not been treated with a blocking agent prior to said contacting, and
(c) determining said immediately visually detectable particle on said porous nitrocellulose test carrier as a determination of said analyte.

30. Method of claim 29, wherein said immediately visually detectable particle is a colored particle.

31. Method of claim 30, wherein said colored particle is a latex particle.

32. Method of claim 29, wherein at least one of said first and second binding partners is an antibody.

33. Method of claim 29, wherein said second binding partner is in the form of a lyophilisate.

34. Method of claim 29, wherein said porous nitrocellulose carrier comprises pores having an average diameter of from about 1 μm to about 12 μm.

35. Method of claim 34, wherein said pores have an average diameter of from about 3 μm to about 10 μm.

36. Method of claim 29, wherein said first binding partner is impregnated in said porous nitrocellulose test carrier at a density of from abut 0.05 ug to about 0.10 ug/cm$^2$ of surface area of said three dimensional configuration.

37. Method of claim 30, wherein said colored particle has a diameter of from about 0.1 to about 0.4 μm.

38. Method of claim 37, wherein said colored particle has an average diameter of about 0.2 μm.

39. Method of claim 29, wherein said porous nitrocellulose test carrier has a front side and a back side, and each side is impregnated with at least one binding partner.

40. Method of claim 27, wherein said analyte is a protein, presence of which in said sample is indicative of a cardiac irregularity.

41. Method of claim 40, wherein said protein is an isoform of troponin.

42. Method of claim 41, wherein said isoform is troponin T.

43. Method of claim 29, comprising determining said analyte in five minutes or less from combining said sample and said binding agent.

* * * * *